United States Patent
De Waleffe

(10) Patent No.: US 11,560,265 B2
(45) Date of Patent: Jan. 24, 2023

(54) PACKING FILM WITH A TOP LAYER FORMING A PREDEFINED OPENING TRACK

(71) Applicant: Xavier De Waleffe, Montigny-le-Tilleul (BE)

(72) Inventor: Xavier De Waleffe, Montigny-le-Tilleul (BE)

( * ) Notice: Subject to any disclaimer, the term of this patent is extended or adjusted under 35 U.S.C. 154(b) by 854 days.

(21) Appl. No.: 16/335,154

(22) PCT Filed: Sep. 19, 2017

(86) PCT No.: PCT/EP2017/073630
§ 371 (c)(1),
(2) Date: Mar. 20, 2019

(87) PCT Pub. No.: WO2018/054899
PCT Pub. Date: Mar. 29, 2018

(65) Prior Publication Data
US 2019/0276213 A1    Sep. 12, 2019

(30) Foreign Application Priority Data
Sep. 20, 2016   (LU) .................................. LU93227

(51) Int. Cl.
| | | |
|---|---|---|
| B65D 75/68 | (2006.01) | |
| A61F 6/00 | (2006.01) | |
| B65D 65/40 | (2006.01) | |
| B65D 75/30 | (2006.01) | |
| B65D 75/58 | (2006.01) | |

(Continued)

(52) U.S. Cl.
CPC .............. B65D 75/68 (2013.01); A61F 6/005 (2013.01); B32B 3/085 (2013.01); B32B 3/266 (2013.01);

(Continued)

(58) Field of Classification Search
CPC .......... B32B 2307/582; B32B 2439/00; B32B 37/12; B32B 3/086; B32B 3/266;
(Continued)

(56) References Cited

U.S. PATENT DOCUMENTS

| | | |
|---|---|---|
| 2,968,391 A | 1/1961 | Sparks |
| 2,991,000 A | 7/1961 | Spees |

(Continued)

FOREIGN PATENT DOCUMENTS

| | | | | |
|---|---|---|---|---|
| GB | 853925 A | 11/1960 | | |
| JP | 05246431 A | * 9/1993 | ............. | B65D 5/708 |
| WO | 2011057931 A1 | 5/2011 | | |

OTHER PUBLICATIONS

International Search Report dated Jan. 5, 2018 from Int'l Appl. No. PCT/EP2017/073630.

*Primary Examiner* — Lee E Sanderson
(74) *Attorney, Agent, or Firm* — James E. Walton

(57) ABSTRACT

The invention is directed to a packaging film (2) comprising: a top layer (4) with at least one aperture (4.1); a bottom layer (8) adhered to the top layer (4); a tear layer (6) adhered to the bottom layer (8) and extending along the at least one aperture (4.1) so that upon traction on the tear layer, said layer tears the bottom layer (8) through the aperture(s) (4.1). The tear layer (6) extends beyond the at least one aperture (4.1), between the top layer (4) and the bottom layer (8), preferably longitudinally in two opposite directions. The invention also relates to a condom wrapping with such a film and to the manufacturing method for such a film.

20 Claims, 6 Drawing Sheets

(51) Int. Cl.
*B32B 3/08* (2006.01)
*B32B 3/26* (2006.01)
*B32B 37/12* (2006.01)

(52) U.S. Cl.
CPC .............. *B32B 37/12* (2013.01); *B65D 65/40* (2013.01); *B65D 75/30* (2013.01); *B65D 75/5838* (2013.01); *B32B 2307/582* (2013.01); *B32B 2439/00* (2013.01)

(58) Field of Classification Search
CPC .... B65D 75/30; B65D 75/68; B65D 75/5827; B65D 75/5833; B65D 75/5838; B65D 75/5894; B65D 65/40; B65D 5/70; B65D 5/708; B65D 2575/586; B65D 31/02; B65D 5/1027; A61F 6/005; Y10S 128/24
USPC ........ 220/259, 260; 383/66, 205; 229/123.1, 229/123.2; 53/133.3, 133.5, 133.6, 133.7; 428/35.7
See application file for complete search history.

(56) References Cited

U.S. PATENT DOCUMENTS

| | | | |
|---|---|---|---|
| 3,720,303 A | | 3/1973 | Giaque |
| 4,405,056 A | * | 9/1983 | Patterson ............. B65D 17/505 220/255.1 |
| 4,595,116 A | * | 6/1986 | Carlsson ................ B65D 5/708 220/359.3 |
| 4,781,323 A | * | 11/1988 | Elias ...................... B65D 5/708 229/123.2 |
| 5,303,838 A | * | 4/1994 | Luch .................... B65D 17/506 220/276 |
| 5,310,262 A | * | 5/1994 | Robison ................. B65D 31/02 383/66 |
| 2005/0144141 A1 | | 6/2005 | Nagao |
| 2014/0209606 A1 | * | 7/2014 | Kearney ............. B65D 75/5838 220/266 |
| 2015/0144141 A1 | * | 5/2015 | Mo .................... B65D 75/5838 206/69 |

* cited by examiner

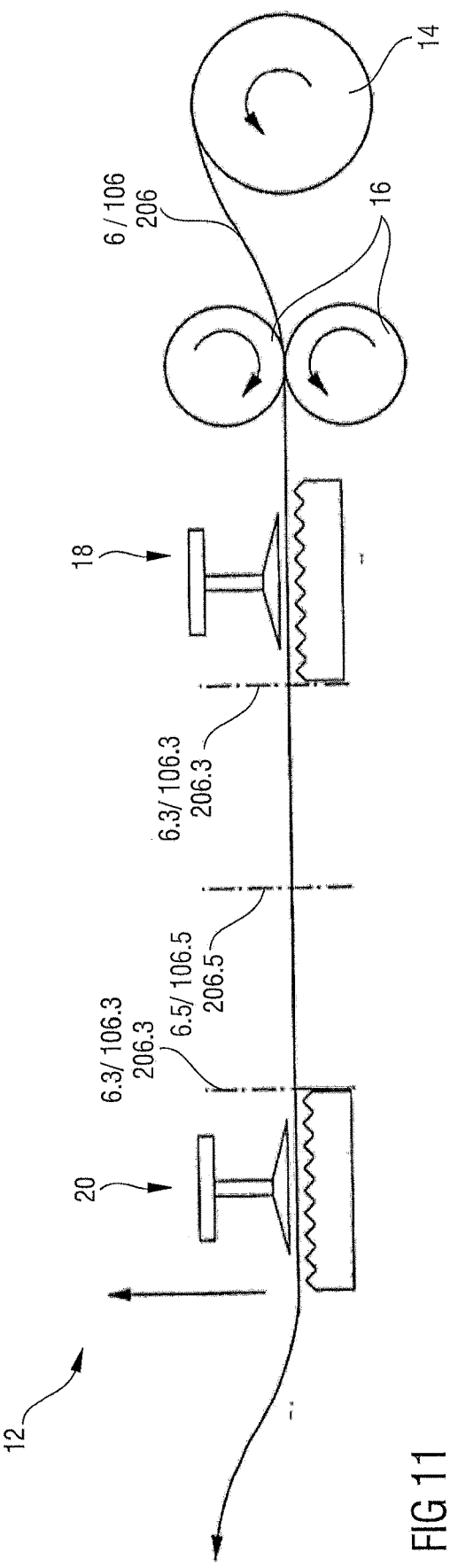
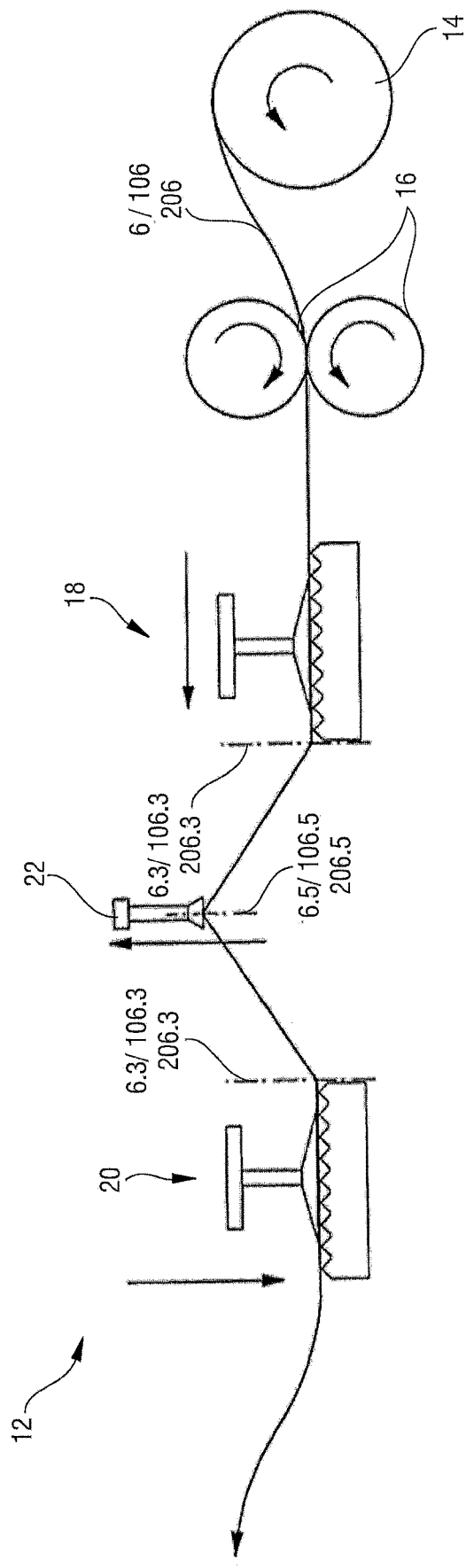

PACKING FILM WITH A TOP LAYER FORMING A PREDEFINED OPENING TRACK

TECHNICAL FIELD

The invention is directed to the field for packaging film, in particular packaging film with predefined opening tracks.

BACKGROUND ART

Prior art patent document published U.S. Pat. No. 2,991,000 discloses a film according to the preamble of claim 1. This film is employed to form a bag or a pouch. The film is made of a first layer (12) comprising an opening (22). On the inner side of the opening (22), the layer (12) is provided with an unsupported strip (24) to cover the opening. A tear seal (18) is applied on the outer side of the opening (22) and is adhered to the unsupported strip (24). The tear seal is made of a layer and of flaps that can be grasped by the fingers of a user. To open the pouch, the user grasps the tear seal (18) and pulls it. The unsupported strip (24) is teared off and the pouch is therefore opened. This film allows a quick opening of the pouch. This film is very beneficial in terms of manufacturing process, since it can be made from a laminated film with several openings arranged in a row and a common tear seal that can extend over the several openings. The film is then cut to the desired dimension which correspond to the dimension of a pouch.

The opening of this document is mostly extending in one direction, i.e. a slotted opening. Such an opening is however only adapted for a pouch that contains an article that can be extracted through such a slotted opening, for instance by grasping an edge of the article. The film of this document is not appropriate when the pouch shall contain articles for which a wide opening, i.e. extending substantially in two dimensions, is needed, for instance when a substantially flat article is to be grasped and handled at the centre of one of its face instead of being grasped at one of its edges.

In addition, the unsupported strip is a single layer of thermoplastic such as polyethylene or polyvinyl whereas the tear seal is a laminate that contains a paper or/and a metal foil. In other words, the unsupported strip needs to be substantially weaker than the tear seal and also the first layer forming the opening in order to properly tear while pulling on the tear strip.

An example of articles that require a two-dimensional opening is condoms. The purpose of grasping condoms at their centre rather than at their edge is to maintain their orientation while handling them between the package and intercourse. This is illustrated in the documents WO2011/057931 A1 and US 2015/0144141 A1. Both of these documents disclose a condom package with a tear-off section that makes it possible to open an aperture extending substantially in two dimensions. The tear-off section is removed when a user pulls a pull tab. These articles however are complex to manufacture because each package individually must be provided with a pull tab and also because of the films that are strong laminate with a metal foil. The condoms have to be protected from external light, leakages, and other kinds of aggression so that the metal foil of the films must be continuous so as to form a closed container. The above pouch film is therefore not suitable for wrappings that requires a laminate to be torn for opening, like a condom wrapping.

SUMMARY OF INVENTION

Technical Problem

The invention has for technical problem to provide a film for packaging which allows an easy manufacturing process and is more flexible for what concerns the integrity of the film and also the article that the package can contain, in particular by making it possible for articles contained in such a package to be grasped in their central portion.

Technical Solution

The invention is directed to a packaging film comprising a top layer with at least one aperture, a bottom layer adhered to the top layer, a tear layer adhered to the bottom layer and extending along the at least one aperture so that upon traction on the tear layer, said layer tears the bottom layer through the aperture(s). The packaging film of the invention is characterized in that the tear layer extends beyond the at least one aperture, between the top layer and the bottom layer, preferably longitudinally in two opposite directions. The bottom layer tears along the contour of the tear layer in the aperture.

The bottom layer is advantageously continuous, i.e. free of any kind of weakening that would modify the integrity of the material of said layer, in particular along the contour of the aperture(s) and the contour of the tear layer in said aperture(s).

By providing a tear layer that is at least partially intermediate the top and bottom layer and that extend beyond the aperture, it is possible to manufacture the package more easily: several layers are assembled and then the final product can be cut to the desired dimensions. Such a film has further the advantage of allowing various forms of two-dimensional openings. By "two-dimensional opening", we mean an aperture that extend substantially in two directions and does not extend mainly in one direction and tenths of times less in the other direction.

According to a preferred embodiment the tear layer is weakened along a portion of contour of the at least one aperture so as to break and separate when exerting traction on the tear layer. This feature allows a clean cut when the tear layer is pulled. The weakening can be achieved by various methods, including perforating and laser weakening.

Preferably, the tear layer comprises a pull tab that is unitary with the tear layer and is formed by a portion of said tear layer that is folded on itself.

By providing an integration of a pull tab into the tear layer, a small number of parts is required to manufacture the film. In this preferred embodiment, the portion of tear layer folded on itself and forming the pull tab may optionally be adhered to each other and may be preferably embossed so as to form a gripping relief structure. Optionally, the pull tab forms a hinge with a portion of tear layer that is adhered to the lower layer in the at least one aperture, said hinge being formed by two adjacent folds of the tear layer portion folded on itself, with said adhered portion.

According to a preferred embodiment, the portion of tear layer that is adhered to the lower layer in the at least one aperture is formed by two sub-portions which are juxtaposed by folding the portion forming the pull tab.

As a preferred embodiment, the pull tab is linked to the portion of tear layer that is adhered to the lower layer in the at least one aperture at a position of said portion that is distant from the contour of said aperture, said distance being preferably comprised between ⅙ and ¼ of the width of said aperture along a pulling direction of said pull tab. This facilitate the handling of the pull tab by the user and allows the top layer to remain undamaged once the pull tab has been pulled.

According to a preferred embodiment, the portion of tear layer that is adhered to the lower layer in the at least one aperture overlaps with the top layer, preferably by a distance d that is comprised between 0.1 mm and 5 mm, more preferably between 0.2 mm and 2 mm. The overlap can vary along the contour of the aperture(s). In that case, the above values are for the maximum distance d along said contour.

In a preferred embodiment, the pull tab extends through the aperture.

In a preferred embodiment, the apertures and pull tabs are distributed longitudinally evenly, the tear layer forming a continuous strip along said apertures, the packaging film being preferably rolled on a mandrel.

In a preferred embodiment, the film comprises a pull tab which is adhered to the tear layer.

In a preferred embodiment, the pull tab is a portion of the top layer corresponding to the aperture.

In a preferred embodiment, the pull tab is adhered to the tear layer only over a portion of said pull tab so as to leave another portion for grasping.

In a preferred embodiment, the tear layer is weakened along a contour that corresponds to the at least one aperture.

In a preferred embodiment, the tear layer has an external contour that corresponds to the at least one aperture and the pulling means extends through said aperture(s).

According to a preferred embodiment, the tear layer is a strip of material, preferably of tear resistant material.

Optionally, the at least one aperture is circular or oval. This is particularly advantageous when the article contained in the package has a general shape that is circular or oval. When the shape of the aperture matches the shape of the article in the package, neither the package nor the article can be damaged when the article is extracted out of the package.

Preferably, the top layer is thicker and/or more resistant than the bottom layer. This allows the top layer to remain unaltered when the pull tab is pulled.

In a preferred embodiment, the bottom layer is a laminate with an impermeable plastic sheet and/or an aluminium sheet. Some articles require a package with particular requirements, like insulation from external elements or sealing, for instance. The bottom layer is therefore chosen in accordance with the requirements of the article to be packaged. Other materials can be foreseen.

The invention applies in particular to condom packages. A preferred embodiment consists in a condom wrapping comprising two superimposed sections of packaging film joined at the edges to form a container housing a condom in a rolled-up state with a condom vessel in a normal position adjacent to one of the two sections of film, the normal direction of unrolling the condom being towards the other section of film, the section of film adjacent to the vessel being in according with one of above-mentioned the examples.

Preferably, the contour of the aperture is in a general shape corresponding approximately to the contour of the condom, the mean diameter of the contour of the aperture being smaller than that of the contour of the condom, in such a way as to ensure the retention of the condom in the condom wrapping after opening, whilst permitting easy extraction thereof, without unrolling, by drawing upwardly the condom vessel.

The invention also concerns a method for manufacturing a packaging film according to any one of the above-mentioned embodiments, comprising in particular the steps of (a) forming the pull tabs unitary with a strip of the tear layer by folding on itself and adhering portions of said strip at regular intervals; and (b) inserting the strip of tear layer with the pull tabs between the top layer and the lower layer by bringing into register the pull tabs and the apertures, and adhering said strip to said lower layer. The simplicity of the manufacturing process results from the particular design of the packaging film.

Optionally, step (a) comprises embossing a gripping relief structure on the strip portions forming the pull tabs. This step ensures the adherence of the two flaps forming the pull tab not only during the manufacturing process but also in use.

In a preferred embodiment, step (b) comprises bringing the pull tabs into the corresponding apertures of the top layer by applying a gas stream, preferably by generating vacuum in front of the apertures. This step of the manufacturing process ensures that the pull tab is easily reachable by the user.

The packaging film and corresponding manufacturing method can have many applications for many different kinds of containers. For instance, applications for packaging of condoms or any flat annular-shaped article, powder of any form, size or shape, pet food, beverage, detergent. The packaging of articles for which the orientation matters can benefit from this technology, in particular in assembling line where an operator must quickly position a part on a device, for instance a cap or a nut. The invention allows to ensure the proper orientation of the content of the package, in a hygienic and reliable controlled way. This can be essential for a medical device that must be handled with care prior to applying to a patient, in particular during an operation.

Advantages of the Invention

The invention is particularly interesting in that it combines several benefits, i.e. possibility of properly tear-opening a strong film, ease to manufacture and flexible as to what article the package can contain, Devices that present one of these advantages independently might be known, but by the very particular design of our invention we manage to combine both advantages without the accompanying drawbacks.

BRIEF DESCRIPTION OF THE DRAWINGS

FIGS. 10 to 12 depict the successive steps of manufacture of a packaging film according to the invention;

DESCRIPTION OF AN EMBODIMENT

Figure 1:
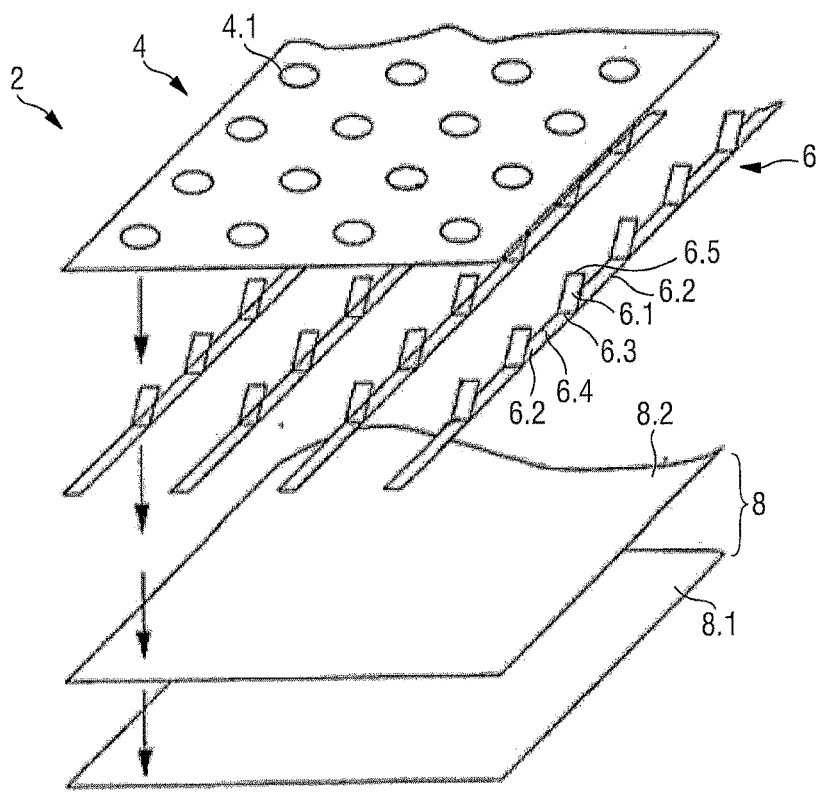
FIG. 1 shows an exploded view of the packaging film according to a first embodiment of the invention.
Figure 2:
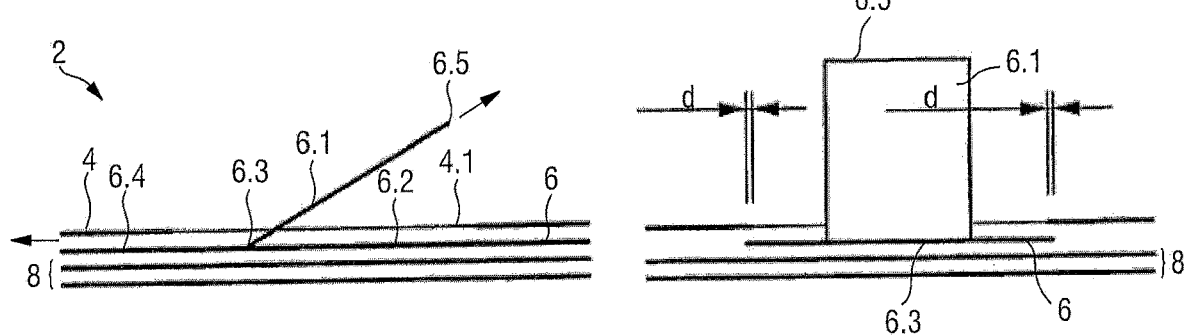
FIG. 2 shows two perpendicular cross sectional views of the packaging film according to the first embodiment of the invention.

FIGS. 1 and 2 illustrate a first embodiment of packaging film of the invention.

FIG. 1 shows an exploded view of the components of the packaging film according to a first embodiment. The packaging film 2 is made of multiple layers. The packaging film 2 comprises a top layer 4 with apertures 4.1. The top layer 4 is continuous and preferably untearable. It can be die cut mechanically or by laser techniques.

Directly below the top layer 4, a tear layer 6 is provided. It consists in this example of a strip comprising a series of pull tabs 6.1 and elongated portions 6.2 that are adhered to a bottom layer 8. Each pull tab 6.1 forms a hinge 6.3 with the portion 6.2. Each portion 6.2 is also weakened transversely 6.4 so as to allow a separation of the strip wen exerting a traction on the corresponding pull tab 6.1. Each pull tab 6.1 can be formed by folding on itself a portion of the strip, the free end 6.5 of said pull tab 6.1 corresponding to the fold of said portion.

The bottom layer 8 can be made of a continuous material. The bottom layer 8 can be made of a plastic layer 8.1 and a metal layer 8.2, such as Aluminium. The strip 6 has preferably one or more of the following properties: continuous, untearable, low elasticity, adhesive, foldable, ability to be carved, maybe covered by Aluminium and/or weldable.

FIG. 2 depicts two perpendicular cross sectional views of the packaging film of FIG. 1 when the components are assembled. The strip 6 is folded on itself to form the pull tab 6.1, and the hinge 6.3. The portions 6.2 of the strip 6 that is not the pull tab 6.1 adhere to the bottom layer 8. The pull tab 6.1 extends through the aperture 4.1 and is therefore reachable by the user. The weakening 6.4 of the strip 6 is essentially at the level of the contour of the opening 4.1 in the first layer, on the opposite side to the direction of traction on the pull tab 6.1 in order to allow a separation of the strip upon traction on said pull tab. The weakening 6.4 can be made by various methods, including perforating, partially cutting and/or laser etching. The direction of traction on the pull tab is illustrated by a first arrow in the left view of FIG. 2, oriented essentially in the plane of said pull tab 6.1 (as illustrated in FIG. 2) and oriented towards the free end 6.5 of said pull tab. A second arrow in the left view of FIG. 2 illustrates the counter effort to be applied to the film 2, counterbalancing the traction on the pull tab 6.1.

Still with reference with FIG. 2, in particular the right view of FIG. 2, the portion 6.2 of the strip 6 that is adhered to the bottom layer 8 and located in the aperture 4.1 can show a slight overlap d with the top layer 4. This overlap is interesting in that it hides below the top layer 4 the edge of the bottom layer 8 that will be torn by traction on the pull tab 6.1. The tearing of the bottom layer 8 can indeed show some irregularities, depending on the material of said layer. Hiding this edge below the top layer 4 can therefore be useful. In addition, it allows avoid also the appearance, along the contour of the aperture 4.1, of portions of the top surface of the bottom layer when the strip 6 is not perfectly positioned in register with the aperture, due to inherent manufacturing tolerances. The overlap d can be comprised between 0.1 and 5 mm, preferably between 0.2 and 2 mm.

The packaging film 2 of FIGS. 1 and 2 can be used for various packaging applications such as pouches and condom wrapping. The condom wrapping can be made of two superimposed sections of packaging film joined at the edges to form a container housing a condom in a rolled-up state. The section of film that is adjacent to the vessel of the condom, i.e. opposed to the normal direction of unrolling the condom, is then made of the film of FIGS. 1 and 2. The contour of the opening 4.1 in the first layer 4 corresponds then approximately to the contour of the condom, so that upon traction on the pull tab 6.1, the second layer 8 is pulled and torn through the aperture 4.1 and opens the wrapping, providing access to the condom.

Figure 3:
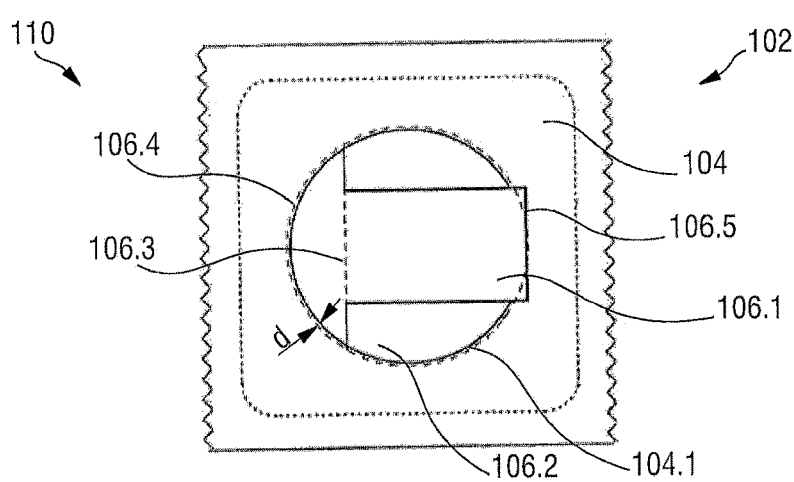
FIGS. 3 to 5 show a top view of a package with a packaging film according to a second embodiment of the invention and the respective tear layer.
Figure 4:
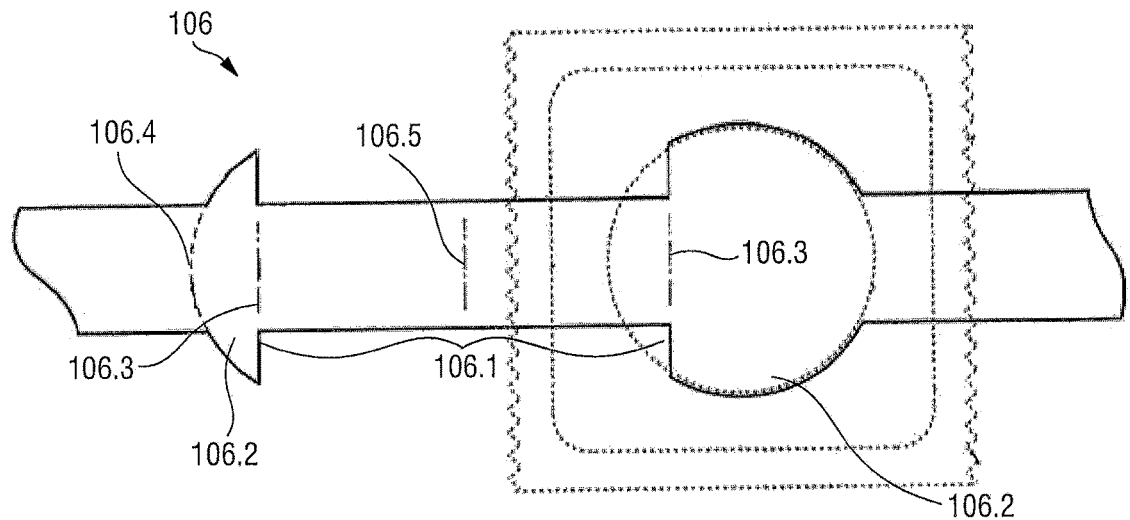
Figure 5:
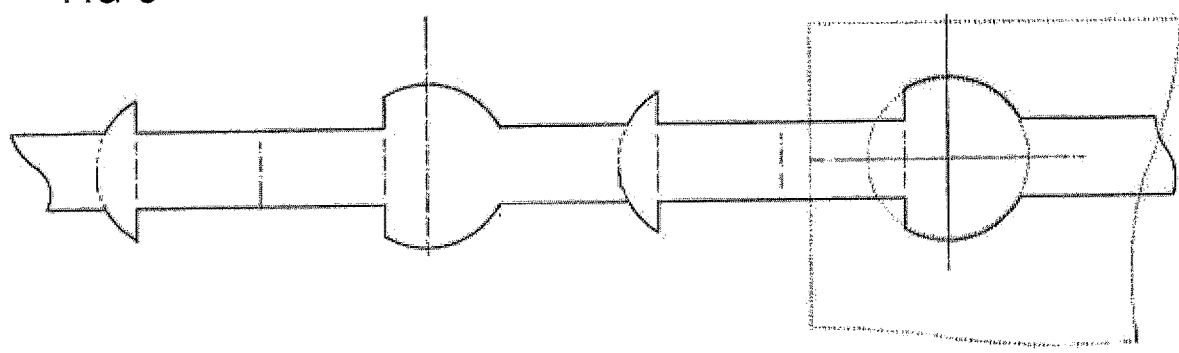

FIGS. 3 to 5 illustrate a second embodiment of packaging film and condom wrapping of the invention. Reference numbers of the first embodiments are used in the second embodiment for designating the same or corresponding elements, these numbers being however incremented by 100. Reference is made to the description of these elements in the first embodiment. Specific numbers comprised between 100 and 200 are used for specific elements.

FIG. 3 is a top view of a condom wrapping 100, similar to the above condom wrapping of the first embodiment where however the section of film 102 that is adjacent to the vessel of the condom, i.e. opposed to the normal direction of unrolling the condom, is made with a tear layer strip 106 that is different from the one of the first embodiment. The top layer 104 and bottom layer can remain essentially identical.

The possible overlap of the strip 106 with the top layer 104, already described in relation with FIG. 2, is also visible in FIG. 3, illustrated by the slight distance d between the contour of the aperture 104.1 and the contour of the corresponding portion 106.2 of the strip.

FIGS. 4 and 5 show the strip before it is folded and its position with respect to the aperture 104.1 of the first layer. The strip is made of several parts that are repeated in cycle along the strip. Two rectangular parts, or adjacent strip portions of the same length, are provided to build up the pull tab 106.1 when folded onto each other. When the ends of these two rectangular parts are folded, they form the hinge 106.3 between the pull tab 106.1 and the rest of the strip 106.2. At both opposite ends of the pull tab 106.1 are provided two partial-disc-shaped portions 106.2. These portions 106.2 aim at building a complete disc, when the pull tab is folded. The disc is preferably slightly larger than the aperture 104.1. The two disc-shaped portions 106.2 are finally connected to each other by the folded pull tab 106.1. The pull tab 106.1 makes it possible to manufacture the packaging that has several neighbouring apertures with a single strip. As a way of example, the pitch of the cycle can be approximately 114 mm, the pull tab being 2 times 27 mm, the length of the disc-shaped portion being respectively 9 and 25 mm. The width of the strip can be around 17 mm. The size of the wrapping can be approximately 60 mm×60 mm. Those are mainly examples and the skilled person would obviously adapt the size of the package to the size of its content. Some condoms are indeed stored in rectangular packages. Their shape in the package is therefore oval. The packaging film of the invention can obviously be adapted to such shape, and many others.

Figure 6:
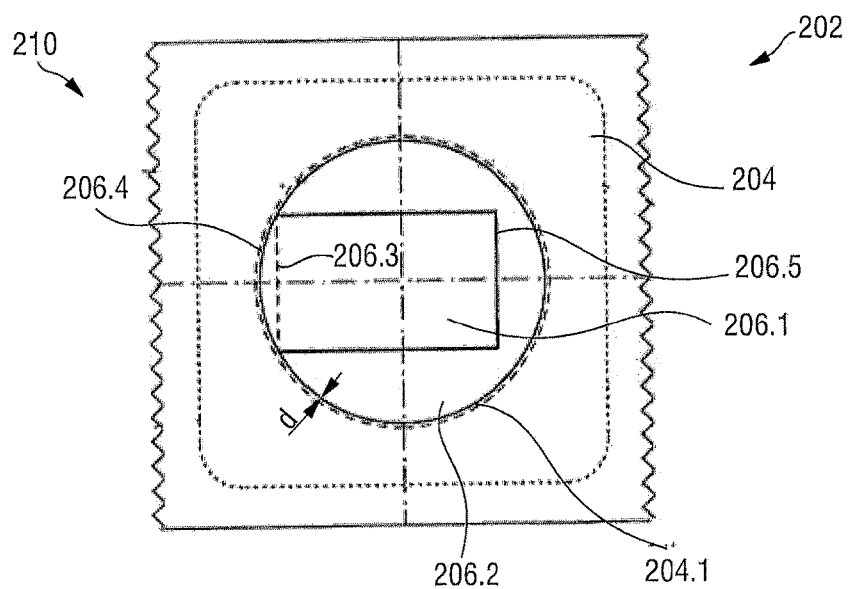
FIGS. 6 to 8 show a top view of another package with a packaging film according to a third embodiment of the invention and the respective tear layer.
Figure 7:
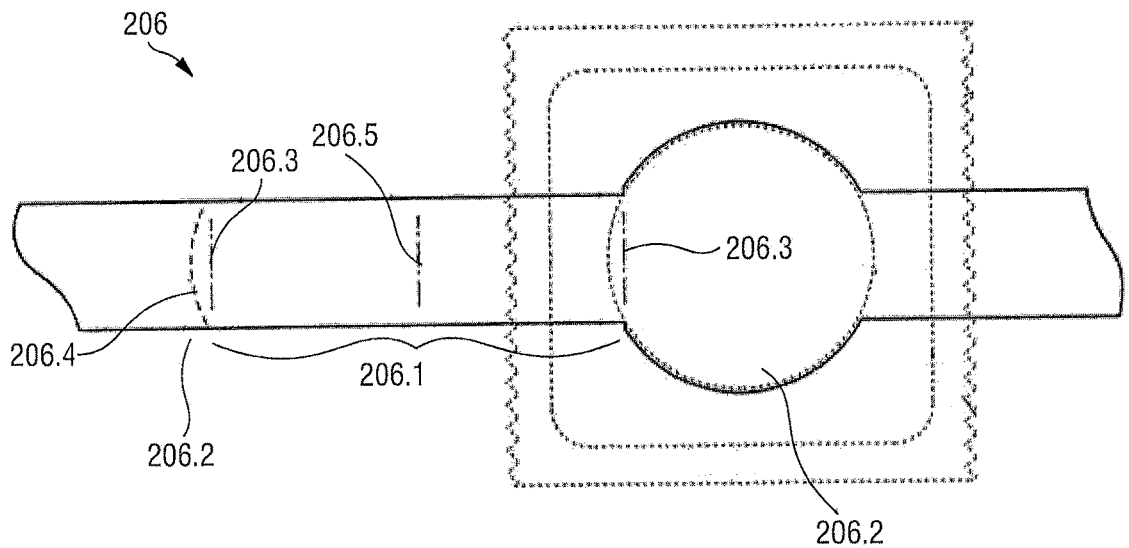
Figure 8:
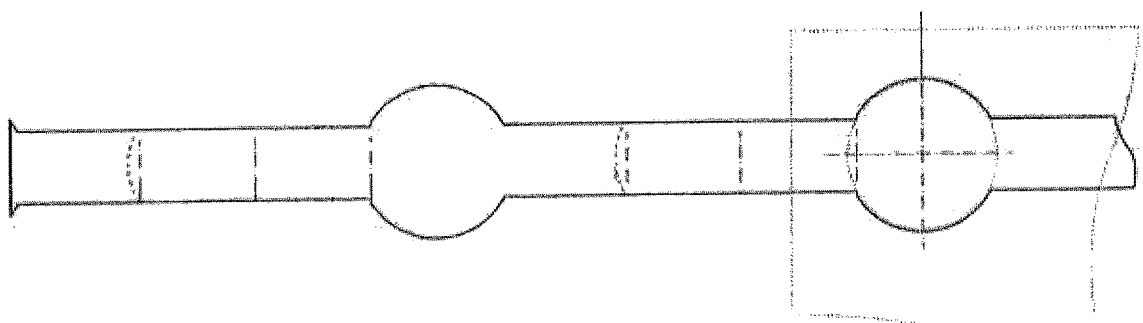

FIGS. 6 to 8 illustrate a third embodiment of packaging film and condom wrapping of the invention. Reference numbers of the second embodiments are used in the third embodiment for designating the same or corresponding elements, these numbers being however incremented by 100. Reference is made to the description of these elements in the first and second embodiments.

This embodiment differs from the second embodiment of FIGS. 3 to 5 in that the portions 206.2 of the strip 206 that correspond to the apertures 204.1 is now readily cut in the strip before forming the pull tabs 206.1 by folding. Also, as visible in FIG. 6, the pull tab 206.1 does not overlap on the top layer 204. This is essentially due to a shifting of the hinge 206.3 of the pull tab 206.1 towards the contour of the aperture 204.1. In this particular example, the pull tab 206.1 has still the same dimensions (17 mm×27 mm).

The possible overlap of the strip 206 with the top layer 208, already described in relation with FIGS. 2 and 3, is also visible in FIG. 6, illustrated by the slight distance d between the contour of the aperture 204.1 and the contour of the corresponding portion 206.2 of the strip.

The examples given in FIGS. 3 to 8 are obviously merely illustrative of the invention and do not limit the scope of protection, be it in terms of dimensions, shapes, or form.

Figure 9:
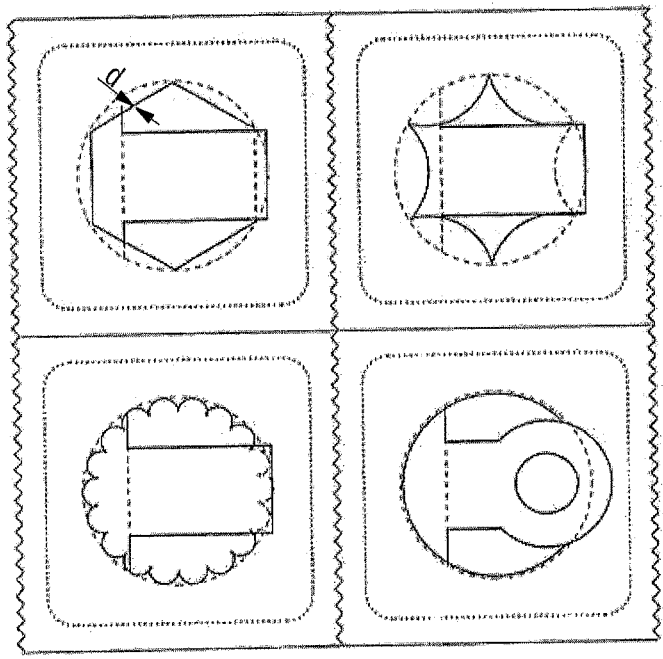
FIG. 9 shows various additional exemplary embodiments of packages with a packaging film according to the invention.

FIG. 9 illustrates possible variants of the shaped of the pull tab and of the portion of the strip located in the aperture of the top layer. The choice of the form can result from commercial choice, or have recreational, educative, legal, political or religious purposes.

With reference to the possible overlap of the strip with the top layer, already described in relation with FIGS. 2, 3 and 6, the overlap d as illustrated in the variants of FIG. 9, can vary along the contour of the aperture in the top layer, in particular when the contour of the tear layer in the aperture has a different shape than the contour of the aperture. The overlap d can vary between 0 mm and 5 mm, preferably between 0 mm and 2 mm.

Other various compositions are possible, but in essence, the principle is to assemble several layers having different properties in terms of mechanical resistance.

One or more of the above-mentioned layers can be printed, for instance for commercial or legal reasons, or be provided with labels.

It is to be noted, that although the examples given to illustrate the invention depict a pull tab, any other pulling means can be foreseen. For instance, a string, a clip, a pin or a tongue can be attached to the tear layer. The connection must in such a case be stronger than the resistance of the bottom layer and the tear layer, such that when the user pulls the string/clip/pin/tongue, the package will open and the attachment between the string/clip/pin/tongue with the tear layer will remain.

Figure 12:
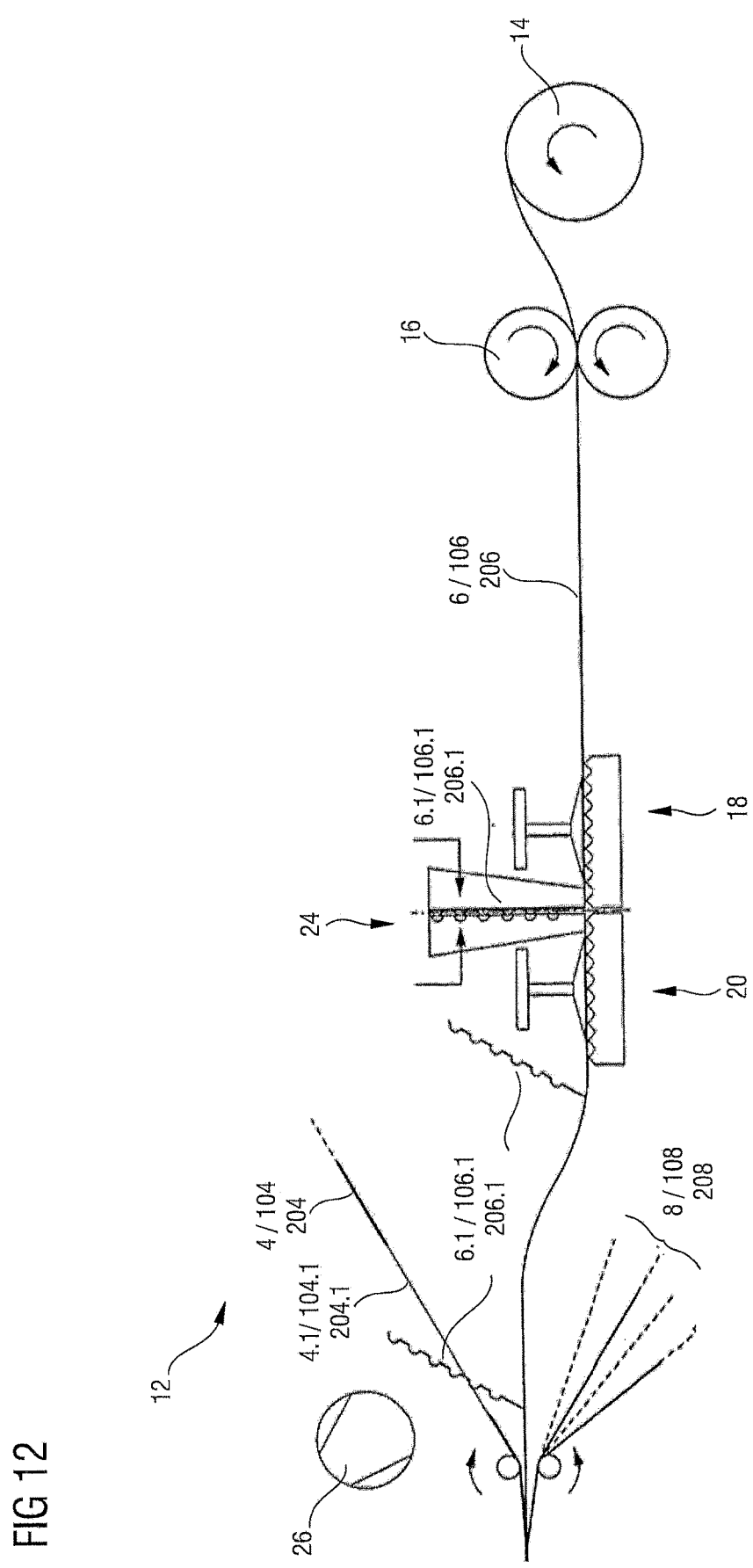

FIGS. 10 to 12 illustrate the successive steps of a preferred embodiment of a method to manufacture a packaging film according to the invention.

FIG. 10 shows the first step. It consists in the unwinding of the tear layer 6 (106, 206) from a coil or roll 14. The layer can be laminated or only unrolled between rollers 16. It is then forwarded to a mobile clamp 18 consisting of a base and a holder. The axes 6.3 (106.3, 206.3), 6.5 (106.5, 206.5) and 6.3 (106.3, 206.3) illustrate the positions of the strip where it will be folded to form the pull tab 6.1 (106.1, 206.1) and the hinge 6.3 (106.3, 206.3). Prior to the folding process, the strip 6 (106, 206) will be clamped on the other side of the folding axes by a fixed clamp 20. Contrary to the mobile clamp 18, the fixed clamp 20 does not move in the direction of unwinding.

As can be seen in FIG. 11, a second mobile clamp 22 lifts up the strip at the point of folding, i.e. axis 6.5 (106.5, 206.5). While the strip is lifted up, the mobile clamps 18 and 22 move towards the fixed clamp 20 and axes 6.3 (106.3, 206.3) which correspond to the folding points on the strip move as well. The clamp 22 moves up until the folding is complete, i.e. when all three axes coincide.

This situation is depicted in FIG. 12. Once this position is reached, a press 24 will weld or at least adhere the folded portion of the strip to form the pull tab 6.1 (106.1, 206.1). The press 24 can also emboss the strip so as to form a relief on the pull tab. A deformation by suction of one of the side only of the pull tab is also possible.

During the step of pressing and/or embossing, the unwinding process can be stopped. Once the pressing/embossing is completed, the strip can again start its unwinding process.

After the pressing/embossing process, the tear layer strip 6 (106, 206) is assembled with the other layers 4 (104, 204) and 8 (108, 208). This can be done by a laminating process between two rollers.

When the pull tab 6.1 (106.1, 206.1) is longer than the aperture 4.1 (104.1, 204.1) and overlaps on the top layer 4 (104, 204), as in the example of FIGS. 3 to 5, it can be convenient to arrange a suction step to ensure that the pull tab is effectively over the top layer. To this effect, a vacuum pump 26 can be provided at the assembling station.

Glue can be applied on the tear layer strip 6 (106, 206) prior to penetrating into the clamps 18, 20, 22. In such a case, the bases of clamps 18 and 20 can be provided with a glue repellent surface. Alternatively, glue may be added after the folding process, prior to the final lamination process.

Figure 13:
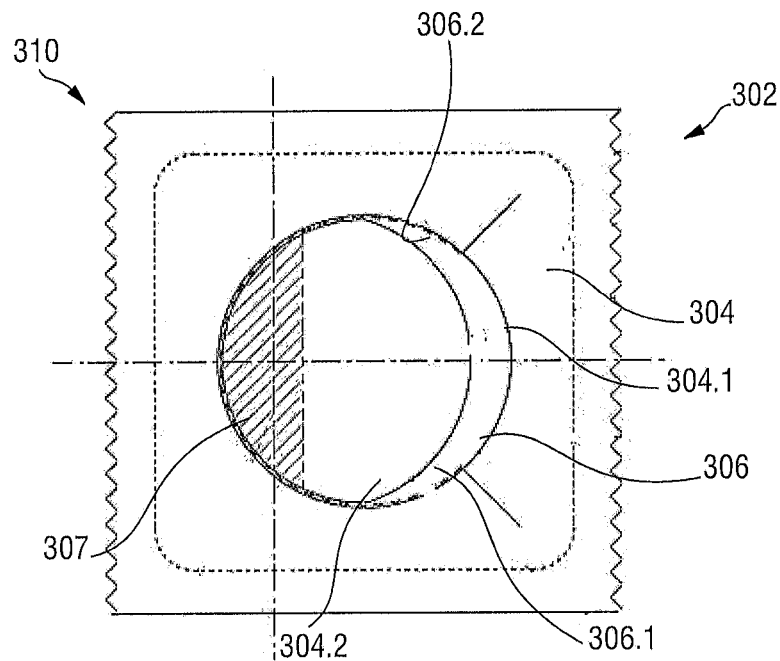
FIG. 13 is a top view of a package with a packaging film according to a fourth embodiment of the invention.
Figure 14:
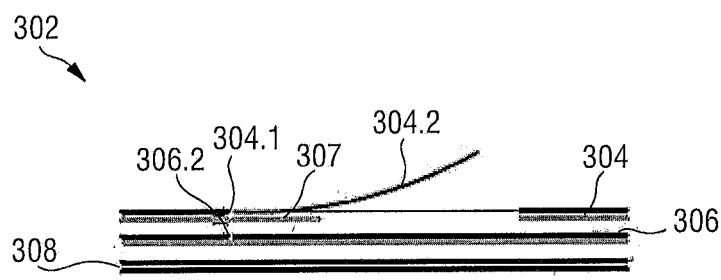
FIG. 14 is a cross-sectional view of the top packaging film of the package of FIG. 15.
Figure 15:
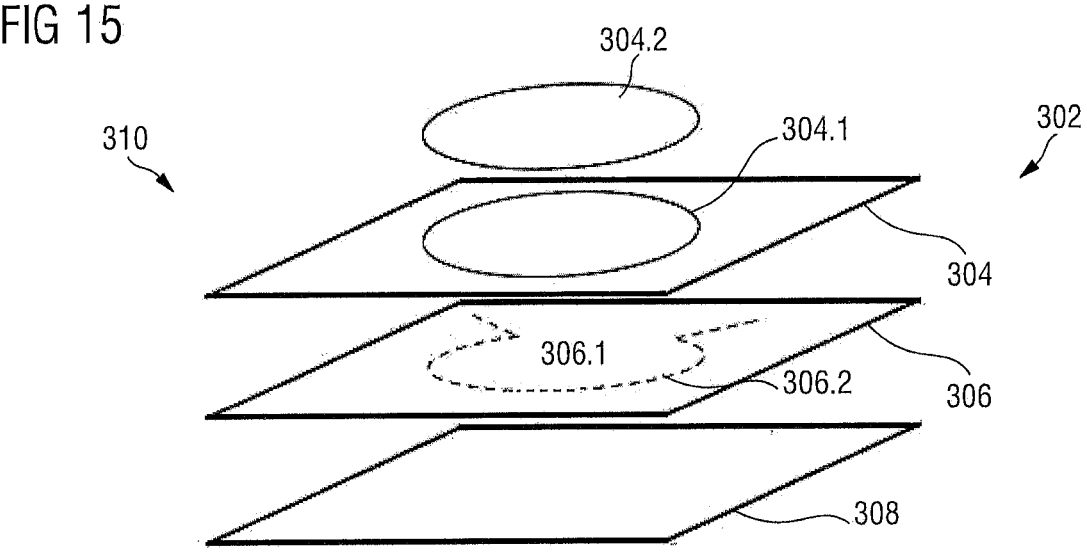
FIG. 15 is an exploded view of the top packaging film of FIGS. 13 and 14.

FIGS. 13 to 15 illustrate a fourth embodiment of a packaging film and a condom wrapping of the invention. Reference numbers of the second embodiments are used in the fourth embodiment for designating the same or corresponding elements, these numbers being however incremented by 200. Reference is made to the description of these elements in the first and second embodiments.

This embodiment differs from the second embodiment of FIGS. 3 to 5 and from the third embodiment of FIGS. 6 to 8, essentially in that the pull tab is not formed by the tear layer anymore but well be a separate element adhered to the tear layer.

More specifically, the tear layer 306 undergoes no folding anymore as in the previous embodiments and the pull tab is formed by a layer portion 304.2 that is adhered, e.g. with glue 307, to a portion of the tear layer 306.1 in the aperture 304.1 formed in the top layer 304. Advantageously, the pull tab is formed by a portion 304.2 of the top layer 304 that corresponds to the aperture 304.1, i.e. resulting from cutting-out said aperture.

The tear layer 306 is weakened or cut along the contour 306.2 which corresponds at least partially to the contour of the aperture 304.1. The weakening or cutting operation is advantageously done before adhesion of the layers 304, 306 and 308.

The pull tab 304.2 comprises a first portion adhered (307) to the portion 306.1 of the tear layer 306 that is in the aperture 304.1 and a second portion for being grasped by the fingers of a user. The first portion is advantageously smaller than the second one. That portion is also advantageously adjacent the contour of the aperture 304.1 and opposed to the second portion with regard to the pull direction.

The invention claimed is:

1. Packaging film comprising:
    a top layer with at least one aperture;
    a bottom layer adhered to the top layer;
    a tear layer adhered to the bottom layer and extending along the at least one aperture so that upon traction on the tear layer said layer tears the bottom layer through the at least one aperture;
    wherein the tear layer extends beyond the at least one aperture, between the top layer and the bottom layer longitudinally in two opposite directions; and
    wherein the tear layer comprises a pull tab which is unitary with the tear layer and formed by a portion of said tear layer that is folded on itself.

2. The packaging film according to claim 1, wherein the tear layer is weakened along a portion of the contour of the at least one aperture so as to break and separate when exerting traction on the tear layer.

3. The packaging film according to claim 1, wherein the portion of tear layer folded on itself and forming the pull tab is embossed so as to form a gripping relief structure.

4. The packaging film according to claim 1, wherein the pull tab forms a hinge with a portion of the tear layer that is adhered to the lower layer in the at least one aperture, said hinge being formed by two adjacent folds of the tear layer portion folded on itself, with said adhered portion.

5. The packaging film according to claim 4, wherein the portion of tear layer that is adhered to the lower layer in the at least one aperture is formed by two sub-portions which are juxtaposed by folding the portion forming the pull tab.

6. The packaging film according to claim 4, wherein the pull tab is linked to the portion of tear layer that is adhered to the lower layer in the at least one aperture at a position of said portion that is distant from the contour of said aperture, said distance being within the range of from $1/6$ to $1/4$ of the width of said aperture along a pulling direction of said pull tab.

7. The packaging film according to claim 4, wherein the portion of tear layer that is adhered to the lower layer in the at least one aperture overlaps with the top layer by a distance d that within the range of from 0.1 mm to 5 mm.

8. The packaging film according to claim 1, wherein the pull tab extends through the aperture.

9. The packaging film according to claim 1, wherein the apertures and pull tabs are distributed longitudinally evenly, the tear layer forming a continuous strip along said apertures, the packaging film being rolled on a mandrel.

10. The packaging film according to claim 1, wherein the film comprises a pull tab which is adhered to the tear layer, the pull tab being a portion of the top layer corresponding to the aperture.

11. The packaging film according to claim 1, wherein the film comprises a pull tab which is adhered to the tear layer, the pull tab being adhered to the tear layer only over a portion of said pull tab so as to leave another portion for grasping.

12. The packaging film according to claim 1, wherein the film comprises a pull tab which is adhered to the tear layer, the tear layer being weakened along a contour that corresponds to the at least one aperture.

13. The packaging film according to claim 1, wherein the tear layer has an external contour that corresponds to the at least one aperture.

14. The packaging film according to claim 1, wherein the tear layer is a strip of tear resistant material.

15. The packaging film according to claim 1, wherein the at least one aperture is circular or oval.

16. The packaging film according to claim 1, wherein the top layer is thicker and/or more resistant than the bottom layer.

17. The packaging film according to claim 1, wherein the bottom layer is a laminate with an impermeable plastic sheet and/or an aluminum sheet.

18. A condom wrapping comprising two superimposed sections of packaging film joined at the edges to form a container housing a condom in a rolled-up state with a condom vessel in a normal position adjacent to one of the two sections of film, the normal direction of unrolling the condom being towards the other section of film, wherein the section of film adjacent to the vessel is a film comprising:
    a top layer with at least one aperture;
    a bottom layer adhered to the top layer;
    a tear layer adhered to the bottom layer and extending along the at least one aperture so that upon traction on the tear layer said layer tears the bottom layer through the at least one aperture;
    wherein the tear layer extends beyond the at least one aperture, between the top layer and the bottom layer longitudinally in two opposite directions.

19. A method for manufacturing a packaging film comprising:
    a top layer with apertures;
    a bottom layer adhered to the top layer;
    a tear layer adhered to the bottom layer and extending along the apertures so that upon traction on the tear layer said layer tears the bottom layer through the apertures;
    wherein the tear layer extends beyond the apertures, between the top layer and the bottom layer longitudinally in two opposite directions;
    wherein the tear layer comprises pull tabs which are unitary with the tear layer and formed by a portion of said tear layer that is folded on itself;
    the method comprising the following steps:
        (a) forming the pull tabs unitary with a strip of the tear layer by folding on itself and adhering portions of said strip at regular intervals;
        (b) inserting the strip of tear layer with the pull tabs between the top layer and the lower layer by bringing into register the pull tabs and the apertures, and adhering portions of said strip to said lower layer.

20. The method according to claim 19, wherein step (a) comprises:
    embossing a gripping relief structure on the strip portions forming the pull tabs, and
    step (b) comprises:
    bringing the pull tabs into the corresponding apertures of the top layer by applying a gas stream in front of said apertures.

\* \* \* \* \*